United States Patent [19]

Russo, deceased et al.

[11] 4,140,161
[45] Feb. 20, 1979

[54] SCREW HOLDING AND DRIVING DEVICE

[75] Inventors: Anthony Russo, deceased, late of Buena Park, Calif.; by Diane Bos, administrator, Diamond Bar; by Robin P. Russo, administrator, La Puente, both of Calif.

[73] Assignee: Minnesota Mining and Manufacturing Company, Saint Paul, Minn.

[21] Appl. No.: 806,664

[22] Filed: Jun. 15, 1977

[51] Int. Cl.² .............................................. B25B 15/00
[52] U.S. Cl. ..................................................... 145/52
[58] Field of Search ........................ 145/52; 144/32 R

[56] References Cited

U.S. PATENT DOCUMENTS

| | | | |
|---|---|---|---|
| 1,644,074 | 10/1927 | Morgan | 145/52 |
| 1,645,753 | 10/1927 | Hanson | 145/52 |
| 2,327,074 | 8/1943 | Snyder | 145/52 X |
| 2,840,126 | 6/1958 | Schmitt | 145/52 X |
| 2,845,968 | 8/1958 | Luber | 145/52 X |
| 2,927,491 | 3/1960 | Bochman | 144/32 X |
| 3,244,208 | 4/1966 | McKenzie | 145/52 |
| 3,298,410 | 1/1967 | Morifuji | 145/52 |
| 3,967,664 | 7/1976 | Lesner et al. | 144/32 R |

FOREIGN PATENT DOCUMENTS

| | | | |
|---|---|---|---|
| 670755 | 8/1929 | France | 145/52 |
| 1189780 | 3/1959 | France | 145/52 |
| 372622 | 11/1963 | Switzerland | 144/32 |
| 258156 | 11/1970 | U.S.S.R. | 144/32 |

Primary Examiner—James L. Jones, Jr.
Assistant Examiner—J. T. Zatarga
Attorney, Agent, or Firm—Cruzan Alexander; Donald M. Sell; Edward T. Okubo

[57] ABSTRACT

The present disclosure relates to a device designed for use in surgical procedures requiring the driving of screws into bone. The device provides positive locking screw holding engagement yet permits angular movement of the screw of up to 10° from the axial direction.

7 Claims, 8 Drawing Figures

SCREW HOLDING AND DRIVING DEVICE

BACKGROUND OF THE INVENTION

The present invention relates to a device for holding screws securely in contact with a driving bit during positioning and driving of the screw. The device is mounted upon a screw driver bit, particularly a bit intended for use in a motor powered driver and more particularly, for surgical procedures involving driving screws into bone.

The device is capable of undergoing repeated steam sterilization without impairment of function, may be quickly disassembled without the need for tools for rapid change of screw driver bit size or style, and is capable of accommodating screws of a variety of sizes and head shapes. The device provides positive, locking screw holding engagement yet permits angular screw displacement of about 10° from axial direction. The device contributes little toward operator fatigue because of its compact size, light weight and use of counter-balanced spring bias forces.

Devices previously used for surgical procedures, primarily bone fixation, although of similar size, operated on a totally different principle. These devices utilized a plurality of spring-like gripping elements each having a forward groove for gripping the screw head. They usually had no, or poor, screw locking means, were prone to malfunction, were subject to frequent premature release of the screw, and provided for little or no angular displacement of the screw from axial alignment so that a screw which was misdirected into a pilot hole could cause cracking or splintering of the bone.

Screw holding devices intended for use by craftsman or in the trades were much more dependable than those used by the surgical profession but were bulky, clumsy and complicated and hence, poorly qualified for adaptation to this highly specialized use. Also, for devices used by a craftsman, equipment cost is a primary concern with little worry directed to possible damage to the screw threads and heads. The damage to screw threads and screw heads caused by these devices is of slight importance in, e.g., sheet metal work but would be of extreme concern in a delicate surgical procedure.

Many of the craft directed prior art devices utilized ball members as well as concentric sleeves, springs, etc. for their gripping action.

Thus, Schmitt U.S. Pat. 2,840,126, although seemingly incorporating many features which are roughly comparable to those of the present invention, differs markedly. Schmitt uses the bit to back up the screw while the balls are forced backward along the screw with possible damage to the screw threads in the process. Further, the device is necessarily fastened onto the motor rather than to the bit because of its large size and weight due partly to the unique screw loading mechanism. Such a mechanism would not only render the device exceedingly clumsy for use in surgical procedures but would also be difficult to clean, disassemble, and sterilize. Schmitt's device appears to have been primarily designed for attachment to a stationary screw-press machine. The device could easily cause scoring or marring of screw heads during engagement, an unacceptable condition for surgical usage. The device also causes positive locking of the screw when loaded, a feature which does not allow any angular movement of the screw to permit compensation for an angularly displaced pilot hole without stressing the substrate. Another disadvantage is that Schmitt's device can only accommodate a given length of screw unless the bit is changed, which necessitates an extensive operation involving the use of tools. Finally, it is doubted whether the device could be used to extract a screw since a screw cannot be engaged by the bit from the front.

Luber, U.S. Pat. No. 2,845,968, is an even more primitive device in that the screw is loosely held by forcing the device forward against the substrate whereby the end of the device, containing balls backed by resilient material, is forced back relative to the bit and screw causing the balls to center the screw. This device would be entirely impractical for exacting surgical work since at no point can the screw be seen for exact positioning. This device would cause damage to both the head and threads of the screw, would be clumsy to use and could hardly be used to extract a screw. The device also would require the use of excessive pressure against a patient causing fatigue to the surgeon.

Taylor, U.S. Pat. No. 3,181,580, is one variation of the many available spring-clip type screw holders. Among the main disadvantages of spring-clip holders are:

(1) They allow for no angular misalignment of the screw from the axial direction.

(2) They are prone to accidental premature release of the screw.

(3) They are usually intolerant of slight screw size changes.

(4) They are prone to fatigue of one or more of the spring elements, a malfunction which is difficult to repair.

(5) They do not have a positive locking mechanism.

McKenzie, U.S. Pat. No. 3,244,208, is another variation of the spring-clip screw holder. This type suffers the further disadvantage that while it can hold flat-head screws such as the sheet metal screws for which it was designed, it has very poor holding power for a screw such as a surgical screw which is designed to fit into a countersunk hole.

Morifuji, U.S. Pat. No. 3,298,410, discloses a simple low cost device for use with a manually operated screwdriver. It does not appear that the resilient holding means can provide the secure locking required for surgical usage with a powered driver.

Eby, U.S. Pat. No. 3,901,298, another spring-clip holder with the disadvantages previously listed, also has the further disadvantage of requiring manual release of the screw as contrasted with the automatic release of the present invention.

Belgium Pat. No. 500,711 relates to a device which requires too much manual dexterity for use in surgical procedures.

Lesner, U.S. Pat. No. 3,967,664, suffers from the disadvantage, common with many of the other prior art patents, that the operator must exert considerable pressure upon the device while driving screws to overcome the spring bias built into the device. For example, the first embodiment described by Lesner requires a driving force counter to the combined action of three heavy springs. This not only causes undue fatigue to the operator but in the case of surgical procedures, would cause entirely unacceptable stress and strain upon the surgical repair site. By contrast, the device of the present invention uses counteracting springs to lessen the overall bias. During the majority of the screw travel there is no spring bias to overcome. During the final screw tightening, there is a very low spring reaction which is almost unnoticeable. Lesner's balls are restricted from penetrating more than a minor amount inwardly toward the screw, restricting gripping power, angular displacement of the screw and the ability of the device to handle screws of various head sizes and shapes. Lesner's device attaches to the driver housing, restricting interchangeability, cleaning and sterilization. The device undergoes very sensitive transition changes within the locking mechanism between loading and driving which would appear to inevitably result in malfunction, particularly if the springs are not proportioned correctly or if the screw is started into an angularly misaligned pilot hole. In the second embodiment, the screw is entirely unlocked from gripping contact during the entire driving operation.

SUMMARY OF THE INVENTION

The device of the present invention is particularly suited for use in surgical procedures involving the driving of screws into bone. The device provides positive locking screw-holding engagement in contact with a driving bit during positioning and driving of the screw. The device is mounted upon a screw driver bit, particularly a bit intended for use with a motor powered driver. As noted, the device of the present invention holds screws securely in contact with a driving bit, yet, due to the unique design of the screw-holding mechanism, the screw is permitted to be displaced about 10° from the axial direction. Thus, if a screw were started in a pilot hole at an angle displaced from normal, the screw-holding and restraining mechanism would permit angular displacement of the screw from the normal axis of the device until realignment of the screw can be accomplished so that the screw can be driven into the hole without causing undue stresses upon the fragile bony substrate, thus avoiding splitting or shattering of the fragile bony substrate. The device is compact in size and light weight, and can be quickly disassembled without tools for rapid change of screw driver bit sizes or styles, and is capable of accommodating screws over a variety of sizes and head shapes.

BRIEF DESCRIPTION OF THE DRAWINGS

In the accompanying drawings which illustrate the invention.

DETAILED DESCRIPTION OF THE INVENTION

Figure 1:
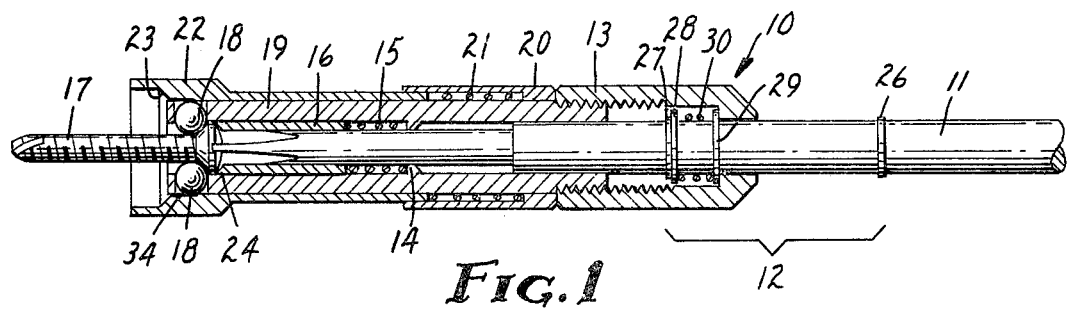
FIG. 1 is an enlarged sectional view of a device of the invention loaded with a screw and ready for operation.

Referring now more particularly to the drawings, device 10 is fastened to a screw-driver bit 11. The bit 11 is shown as a cruciate slotted bit although it should be realized that any type of bit may be used depending, of course, upon the screw type to be driven. A variety of bits would normally be furnished and each of these could carry a screw retaining device 10, as shown, or the bits could be rapidly interchanged to one screw retaining device as will be described later. For simplicity, the bit 11 is shown as having one diameter change throughout its length although it will be understood that the bit can have various changes of diameter throughout its length. Bits for surgical usage will be constructed of stainless steel or other suitable rust-resistant alloy which can take a good finish, maintain a hardened driving edge and withstand repeated steam sterilization. Although the device is described as being fastened to the bit, this terminology is not entirely accurate in that all parts of the device are movable with respect to the bit, the degree of movement being restricted only by the bit retainer 12 and the various locking and biasing means. Again, the bit retainer 12 has been over-simplified for purposes of explanation and will be described more fully later.

The retainer nut 13 is used to fasten the bit 11 to the device. When it becomes necessary to change bits so that different types of screws may be used, the retainer nut 13 may be easily and quickly unscrewed, usually without the need for tools, and after the threaded portions are disengaged, the bit 11 removed from the device, the bit retainer 12 pulling the retainer nut 13 with it. The retainer nut 13 can then be slipped onto a different bit and the bit slipped into the device and the retainer nut quickly tightened. while this method of bit replacement is preferred, it should be understood that the retainer nut may be more or less permanently fastened to the device particularly if the need to change bits is of no concern.

Collet 19 is shown serving both as a bushing for the bit 11, and shoulder 14 thereon acts as the backing restraint for bias spring 15, which bears against the plunger 16, which thereby presses against the head of a screw 17 holding said screw head firmly against balls 18, which in turn are held in place within openings of the collet 19. It is, of course, contemplated that the screw driving bit 11, slightly modified, can be spring biased to bear against the head of screw 17, thus eliminating the need for the separate plunger 16.

In the preferred form of the invention, four balls 18 are used. A lesser or greater number may be used but four seems to provide the best compromise between holding power and angular freedom. With most of the prior art devices, the screw was locked rigidly in axial position so that it tended to be directed wholly by the operator even though such direction might be at an angle displaced from that of the drilled pilot hole, thereby causing undue stresses upon the substrate into which it was being driven. In the case of fragile bone substrates, such misdirection could cause disastrous splitting of the bone. With the present device, the balls 18 hold the head of the screw 17 firmly and in non-releasable security against the pressure of the plunger 16 while still allowing about 10° of angular displacement from the axis of the device.

While restraining means other than balls may be used, spherical balls provide the best restraint for screw heads and provide a certain latitude for restraint of various size screws while also contributing to the smoothness of operation of the device.

It will be seen that the plunger spring 15 acts against the shoulder 14 of collet 19 to bias the plunger 16 which in turn forces the screw head 17 against the balls 18, which are always retained axially within the openings in the collet 19. It will be appreciated that a separate spring retainer 14 could be incorporated as a loose insert held in place against the collet 19. This method of assembly would have the advantage that the device could be easily disassembled into individual components for cleaning and/or sterilization, a particular advantage for surgical tools and instruments. The separate spring retainer 14 should have a fixed relationship to the collet 19 and this fixed relationship can be provided by press fitting them together or through the use of other retaining means such as screw threads, retaining ring, etc.

The exterior of the device is made up of a spring retainer 20, a collet sleeve spring 21 and a collet sleeve 22. The spring retainer 20 can be a loose insert held in place by the retainer nut 13 so that it can be removed when the retainer nut 13 is removed, thereby allowing easy disassembly of the components for cleaning and/or sterilization. As shown, spring retainer 20 is press-fitted to the collet 19 or can be assembled thereto as by screw threads, socket-head screw, retainer ring, or the like.

The spring retainer 20 acts as a stop or backup for the collet sleeve spring 21 which biases the collet sleeve 22 forward against the balls 18. The collet sleeve 22 holds the balls 18 inwardly radially against the screw head and/or screw shank and is restrained from further forward movement in the unlocked position by the action of its inner shoulder 23, against these same balls 18. As can be clearly seen in FIGS. 7 and 8, collet sleeve 22 is provided with a shallow circumferential recess 34 adjacent inner shoulder 23 for the purpose of limiting the forward movement of the collet sleeve 22 in the loaded condition (FIGS. 1 and 4) through the action of balls 18 against said recess 34.

Although the device 10 is free to move axially to some extent relative to the bit 11, there is an interaction between these movements which can best be seen in FIGS. 1 through 6.

Figure 2:
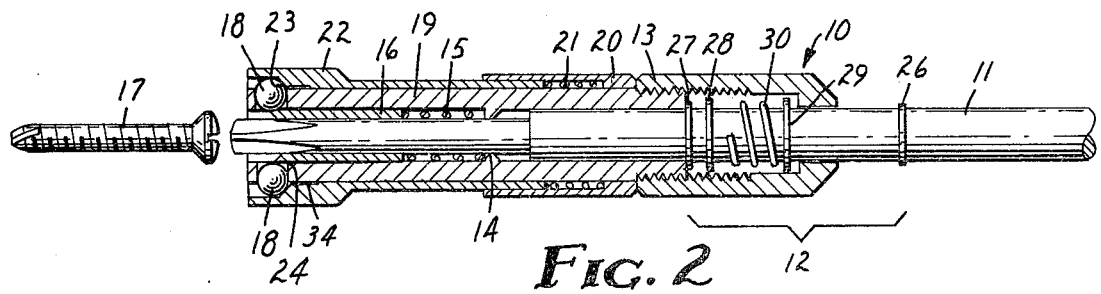
FIG. 2 shows the device in its unlocked form prior to being loaded with a screw.

In the unlocked position shown in FIG. 2, the plunger 16 is in full forward position due to the bias action of the extended plunger spring 15. The plunger 16 is restrained from further forward motion by the action of its outer forward shoulder 24 against the balls 18. Complementarily, this shoulder 24 presses the balls outward of their openings in the collet 19 where they act to retain the collet sleeve 22 in its rearward position against the compressed collet sleeve spring 21.

The bit 11 is also shown in full forward position although it could also be retracted rearwardly, unless biased forward by an additional spring 30 as can be seen in the drawings.

Figure 3:
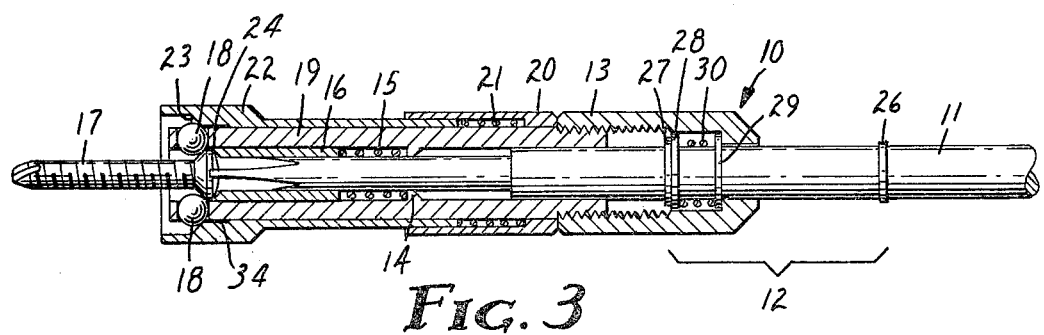
FIG. 3 shows the device approximately midway in the screw loading process.

In FIG. 3, the device 10 is held in one hand, the head of the screw 17 engaged with the bit and the screw then pushed back forcing the plunger 16 and bit 11 backward against spring 15. The plunger 16 is shown in this view depressed almost to the point where the balls 18 can move radially inwardly toward the screw 17.

In the loaded position shown in FIG. 1, the screw has been pushed rearwardly forcing the plunger 16 back and compressing plunger spring 15. As the plunger 16 is pushed back past its position in FIG. 3, the balls 18 are forced inward against the screw 17 by the camming action of the collet sleeve 22 as it is forced forward by the collet sleeve spring 21. The balls 18 act to prevent the collet sleeve 22 from going any further forward than the position shown.

Figure 4:
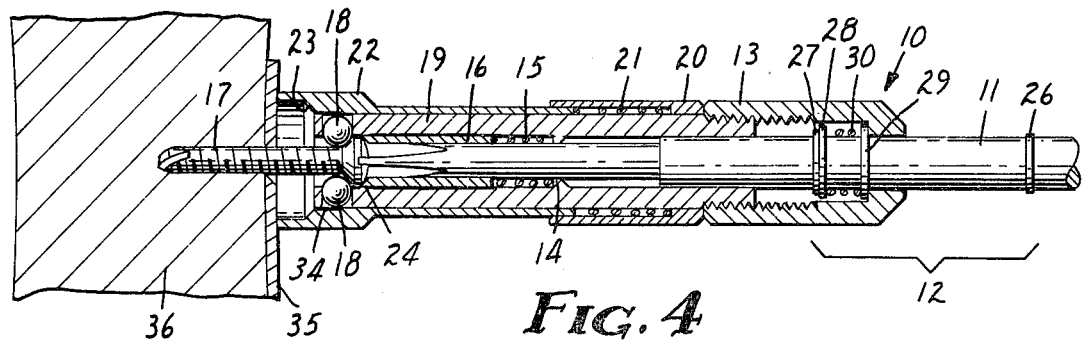
FIG. 4 shows the relationship of the components shortly after the forward edge of the collet has contacted the substrate surface as the screw is driven into place.

The device as shown in FIG. 1 would be used to start driving the screw. The entire device 10 would rotate with the bit 11 and screw 17. This relationship would be maintained until the forward end of the collet sleeve made contact with the substrate surface as shown in FIG. 4, which schematically illustrates the situation in the majority of surgical procedures where bone is held together with screws. A metal plate 35 is placed along and against the fractured bone 36 and surgical screws 17 are then driven into predrilled countersunk holes in the plate and into the bone. It is, of course, understood that in those procedures where a metal plate is not used, the bone would be the substrate against which the collet sleeve would make contact. The collet sleeve 22 has been partially forced back against the biasing action of the collet sleeve spring 21 due to its having been forced against the substrate surface. At this point, collet sleeve 22 is still holding the balls 18 against the screw 17.

Figure 5:
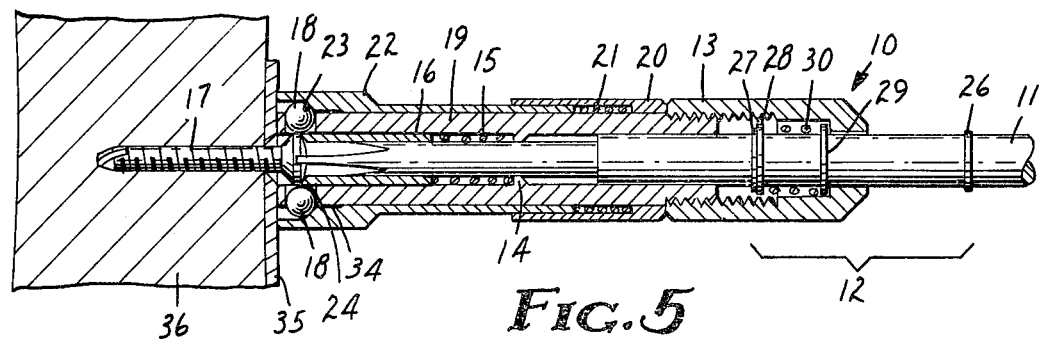
FIG. 5 shows the relationship of the components with the screw driven further into the substrate.

FIG. 5 shows the action as the screw is driven further into the substrate. The collet sleeve 22 has now been forced back fully in relationship to the collet 19 and has allowed the balls 18 to migrate outward radially due to the camming action of the screw head. With the balls 18 thus retracted, the screw head and plunger 16 are allowed to pass the balls 18. The screw 17 is no longer secured between the balls 18 and the plunger 16 but since the screw is almost completely driven in place, such holding action is no longer necessary. The bit 11 is still in contact with the screw head and plunger 16 follows screw 17 because of its spring bias and maintains concentricity of the bit 11 within the slots of the screw head.

Figure 6:
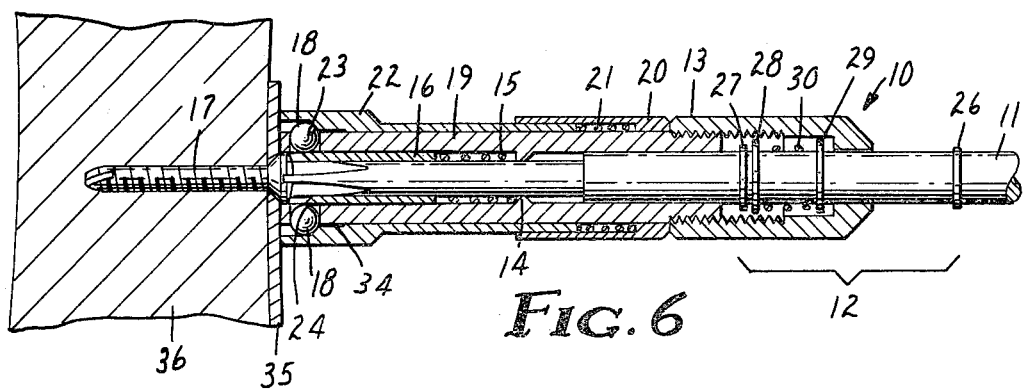
FIG. 6 illustrates the device with the screw fully driven into the substrate.

FIG. 6 shows the situation at the time that the screw 17 is fully driven into place. Under pressure from the operator, the bit 11 has continued to follow the screw. Under pressure from the plunger spring 15, the plunger 16 has also followed the screw and in the process has locked balls 18 into retracted position radially against the collet sleeve 22. The device 10 and bit 11 can now be removed from contact with the screw. The device is locked into unload relationship and is ready to be loaded with another screw as the device is now in the same position as that shown in FIG. 2.

Since during the final driving stages, shown in FIGS. 4, 5 and 6, it is difficult to visualize the exact position of the screw, the bit 11 could be marked to indicate the amount of screw still remaining above the substrate surface. The amount of forward travel of the bit 11 can also be varied by positioning the bit retainer 12 so that the screw can be fully driven as shown or so that the screw could be left protruding a small amount. The final tightening of the screw would then be done manually without the use of the device. The arrangement shown is preferred since it reduces the possibility of marring the screw head during premature disengagement of the bit from the screw head while the bit is still powered.

The spring loading arrangement for bit retainer 12 can be seen in any of FIGS. 1 to 6. Forward split retainer ring 27 and rear split retainer ring 26 keep the spring assembly and the retainer nut 13 in place during disassembly of the device 10. If it should be necessary to remove the retainer nut 13 from the bit 11, it can be firmly pulled rearwardly depressing split retainer ring 26 further into its groove allowing retaining nut 13 to pass over it. Spring retainer bushings 28 and 29 maintain the spring position, transmit forces to the spring, and can similarly be passed over the split retainer ring 26 with firm axial pressure. In use, the spring 30 maintains forward bias on the bit relative to the retainer nut 13 and hence relative to the device 10 so that the bit 11 always remains in contact with the screw head slots, particularly during screw loading thereby eliminating marring of the screw head during the start of driving.

Figure 7:
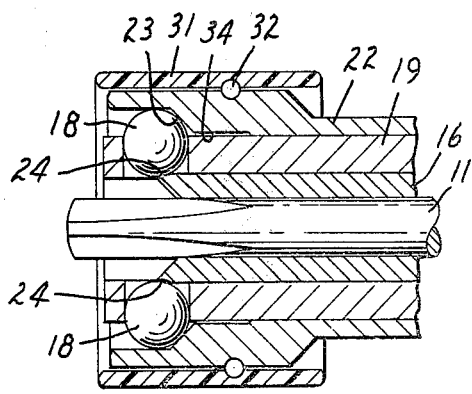
FIG. 7 illustrates another embodiment of the invention.

While a screw 17 is being driven, the device 10 will rotate with the bit 11. The rotational speed is slow enough so as not to cause any safety hazard and in fact the frictional drag between bit 11 and device 10 is so low that the device 10 can easily be held and prevented from rotating. Nevertheless, even slow, low torque rotation can be undesirable in some instances, even possibly causing slight scratching of the substrate from contact with the rotating collet sleeve 22. To further reduce this possibility. FIG. 7 shows an alternative construction having a further outer sleeve 31 which can be mounted over the collet sleeve 22 by means of bearings such as the ball bearings 32.

Figure 8:
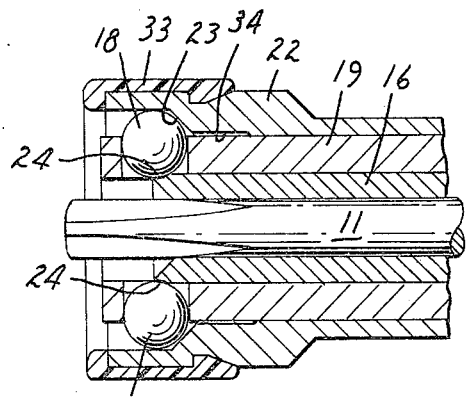
FIG. 8 shows a still further embodiment of a device according to the present invention.

The embodiment shown in FIG. 8 utilizes a "Teflon" extension 33, for the collet sleeve 22. The sleeve 33 can be snapped into place over the collet sleeve 22 as shown and will not only present a low friction mar-proof contact surface but can also rotate relative to the collet sleeve 22 due to its inherent low-friction surface.

What is claimed is:

1. In combination, a screw driving bit having a rearward driving end, a shank and a forward screw engaging end and a screw retaining device movably attached to the shank of said bit, said screw retaining device comprising a collet and a plurality of screw retaining balls disposed within openings equidistantly spaced around the periphery of said collet, said balls being free to move radially in said openings, a spring biased member which, in a first position, biases said balls radially outwardly and which, in a second position, exerts spring pressure against the head of a screw received within said collet, a spring biased collet sleeve which, in a first position, restrains the outward movement of said radially outwardly biased balls and which, in a second position, biases said balls radially inwardly against the shank of said screw thus preventing axial movement of said screw, spring means biasing said screw driving bit into a forward position into engagement with the slot in said screw head thereby further preventing axial movement of said screw and eliminating marring of the screw head in the screw driving process.

2. The combination of claim 1 wherein said spring biased member is a cylindrical plunger.

3. The combination of claim 1 wherein said spring biased member is the screw driving bit.

4. The combination of claim 1 wherein said screw retaining device is carried by the shank of said bit by a retainer nut slidably coupled to said shank by retaining means located on said shank.

5. The combination of claim 4 wherein said retaining means comprises at least one split ring, which, when depressed into its retaining groove in said shank, allows passage of said retainer nut thereover thereby permitting interchangeability of screw driving bits.

6. The combination of claim 1 wherein said screw retaining balls are located within openings in said collet, the maximum diameter of said openings adjacent the interior of said collet being slightly less than the diameter of said balls such that the balls will not pass through said openings into said interior.

7. The combination of claim 6 wherein four screw retaining balls are disposed within openings equidistantly spaced around the periphery of said collet and are constrained by said openings and said collet sleeve.

* * * * *